United States Patent [19]

Moschik

[11] Patent Number: 5,441,408
[45] Date of Patent: Aug. 15, 1995

[54] ORTHODONTIC DEVICE WITH A CERAMIC TOOTH ATTACHMENT

[75] Inventor: Erich Moschik, St. Veit/Glan, Austria

[73] Assignee: Hirsch Advanced Ceramics Gesellschaft m.b.H., Klagenfurt, Austria

[21] Appl. No.: 178,267

[22] PCT Filed: Jul. 9, 1992

[86] PCT No.: PCT/AT92/00088
§ 371 Date: Jan. 3, 1994
§ 102(e) Date: Jan. 3, 1994

[87] PCT Pub. No.: WO93/00865
PCT Pub. Date: Jan. 21, 1993

[30] Foreign Application Priority Data

Jul. 9, 1991 [AT] Austria .................................. 1365/91

[51] Int. Cl.$^6$ .................................................. A61C 3/00
[52] U.S. Cl. .................................................. 433/8; 433/9
[58] Field of Search ................ 433/8, 9, 10, 11, 12, 433/13, 14, 15, 16, 17, 18, 19, 20, 21, 22, 23, 24

[56] References Cited

U.S. PATENT DOCUMENTS

| | | | |
|---|---|---|---|
| 1,976,141 | 10/1934 | Richardson | 29/160.6 |
| 2,045,025 | 6/1936 | Richardson | 29/160.6 |
| 4,302,532 | 11/1981 | Wallshein | 433/8 |
| 4,322,206 | 3/1982 | Reynolds | 433/9 |
| 4,430,061 | 2/1984 | Webb et al. | 433/9 |
| 4,604,057 | 8/1986 | Viglietti | 433/9 |
| 4,948,538 | 8/1990 | Wei et al. | 264/6 |
| 4,954,080 | 9/1990 | Kelly et al. | 433/8 |
| 4,988,293 | 1/1991 | Collins et al. | 433/8 |

FOREIGN PATENT DOCUMENTS 0189540 8/1986 European Pat. Off. .
2559059 8/1985 France .

*Primary Examiner*—Nicholas D. Lucchesi
*Attorney, Agent, or Firm*—Collard & Roe

[57] ABSTRACT

An orthodontic device comprises a ceramic tooth attachment comprising a base body having an in-line transmittance of visible light in the range of 5% to 60% through a thickness of 0.5 mm and the base body consisting of polycrystalline grains comprising a substance selected from the group of high purity zircon, high purity yttrium oxide, lead titanate zirconate and an aluminum oxide, and X-ray visible precipitations arranged on grain boundaries between the polycrystalline grains, the precipitations comprising ytterbium fluoride in a concentration range of 3 to 150 ppm.

19 Claims, 5 Drawing Sheets

ORTHODONTIC DEVICE WITH A CERAMIC TOOTH ATTACHMENT

BACKGROUND OF THE INVENTION

1. Field of the invention

The invention relates to an orthodontic device, with a ceramic tooth attachment of a polycrystalline ceramic structure and various additives with an optical transmittance in the visible spectrum at a thickness of 0.5 mm, in the range of from 5 to 60%.

2. Description of the prior art

In a known orthodontic device—according to U.S. Pat. No. 1,976,141 and U.S. Pat. No. 2,045,025, the tooth attachments are made of stainless steel and secured to a stainless steel band, which encircles the perimeter of the tooth in order to keep the tooth attachment in the right position.

Various other tooth alignment methods and orthodontic devices have been developed in which stainless steel tooth attachments are cemented directly to the surface of the tooth. These methods and devices require no band to secure the tooth attachments. Such systems are used very often. These known tooth alignment methods and devices are known among others from the U.S. Pat. Nos. 4,604,057, 4,430,061 and 4,322,206. The metallic appearance of such stainless steel tooth attachments is a significant drawback. Therefore, for reasons of appearance, especially adult patients desire orthodontic devices, which are not made of metal but of transparent and translucent materials as such materials provide improved cosmetic appearance. Accordingly, transparent plastic materials are used, mostly polycarbonates or transparent or translucent ceramic materials which comprise aluminum oxide. With known tooth attachments made of nonmetallic materials, which are produced in very small sizes in order to keep cosmetic drawbacks at a minimum, it is known—according to U.S. Pat. No. 4,302,532—that the strength of ceramic tooth attachments made of plastic materials is increased by reinforcing elements.

Furthermore, orthodontic devices with a ceramic tooth attachment consisting of a polycrystalline, ceramic structure with various additives are known. A known ceramic tooth attachment—according to U.S. Pat. No. 4,954,080—consists of polycrystalline ceramics with a light transmission in the visible spectrum, which reduces the visibility of this tooth attachment, so that when it is mounted on the tooth, it can be hardly recognized by a third party. This polycrystalline ceramic body for the ceramic tooth attachment is produced by pressing a high purity aluminum oxide powder, which, in the process, is sintered in order to present a close to zero porosity and an average grain size in the range of 10 to 30 micrometers. Preferably, the tooth attachment is colorless. An in-line light transmission in the visible spectrum should be 20 to 60% through a specimen having a thickness of 0.5 mm. The disadvantage with this tooth attachment is that the latter can not be seen when X-rays are made.

However, it is already known—according to EP-PS 0 189 540—that microfilled dental material is being manufactured which presents both, good X-ray opaqueness and at the same time good transparency. This dental material which is used as filling material, dental cement, crown and bridge material, prosthetic material and also for the production of dentures, inlays, implantations and prefabricated parts, consists of polymerized inorganic binders and compositions of rare precious metals and also, if required, further inorganic compositions as filling materials, whereby it may also contain a fluorinated rare-earth metal (elements of atomic number 57-71 of the periodic table of elements) or a mixture of these fluorides. This type of dental material is often mixed to a paste by kneading, which hardens under various conditions, in particular under the effect of light. The light transmission in the visible spectrum for such parts is mostly sufficient, however, when used for tooth attachments of orthodontic devices it was not satisfactory.

SUMMARY OF THE INVENTION

The object of the present invention is to create an orthodontic device with a ceramic tooth attachment having enough light transmission in the visible spectrum so that a third party cannot recognize such a tooth attachment right away and which, on the other hand, is opaque enough for X-rays in order to make such a tooth attachment visible on an X-ray image.

According to the present invention, the orthodontic device comprises a ceramic tooth attachment comprising a base body having an in-line transmittance of visible light in the range of 5% to 60% through a thickness of 0.5 mm and the base body consisting of polycrystalline grains comprising a substance selected from the group of high purity zircon, high purity yttrium oxide, lead titanate zirconate and an aluminum oxide, and X-ray visible precipitations arranged on grain boundaries between the polycrystalline grains, the precipitations comprising ytterbium fluoride in a concentration range of 3 to 150 ppm.

The advantage of this solution derives from the fact that it is now possible to manufacture a tooth attachment which consists of polycrystalline grains, is opaque in order to be rendered visible on X-ray images and resistant against pressure by means of appropriate sintering processes, wherein the X-ray visible precipitations can be produced during the sintering process at the same time the tooth attachment is manufactured, and therefore has a long life span and great strength. It is essential, that by adding to the grain boundaries, X-ray visible precipitations, such as ytterbium fluoride mixed with polycrystalline grains for example, an X-ray opaque material can be achieved, the light transmission of which is not influenced disadvantageously in the visible spectrum. The great advantage of this embodiment however, lies in the fact that when such a tooth attachment or part of such a tooth attachment has been swallowed by accident, the swallowed attachment or attachment part is visible on the X-ray image. It can therefore be traced in the human body at any time to remove it and thus to avoid that sharp ceramic parts or fragments of these ceramic parts lead to inner injuries of the stomach, the intestines, the trachea or the lungs.

Further additives, such as high purity yttrium oxide and/or high purity lanthanum oxide improve the properties of a ceramic tooth attachment. By using yttrium or lanthanum oxide, the strength can be increased at the same time as the processing temperature can be advantageously lowered.

Another development is an average grain size so that the desired surface quality of tooth attachments with sufficient strength is achieved.

If the base body has pores occupying a volume of less than 0.003% of the base body volume, subsequent decoloration of the tooth attachment is prevented.

Further additives allow for greater strength by preventing rapid grain growth.

An improved light transmission is achieved and an optical effect of foreign substance effectively avoided if lithium fluoride is added.

An increase of tenacity is achieved by using a base structure consisting of high purity yttrium oxide and thereby preventing the danger that parts of the orthodontic device, on which tangential forces are exerted by the alignment elements, come off in splinters.

A highly tenacious ceramic base material is achieved if the base structure consists of a mixture of lead titanate zirconate which is modified with lanthanum, ytterbium fluoride and yttrium oxide.

In a further advantageous embodiment the base structure consists of an Al$_2$O$_3$ polycrystalline stabilized zircon ceramic and the additives formed by the yttrium fluoride and lanthanum, whereby the base ceramic presents an improved tenacity and thereby achieves a uniform tension course in the device when tensile forces are taken up.

If the polycrystalline grains form on their grain boundaries together with their X-ray visible precipitations the base body and/or an attachment body of a tooth attachment, which consists at least of two parts, the ceramic part can be detached from the plastic holding and therefore splinter formation can be avoided when it is cracked off the tooth, and only the plastic body is to be taken off the tooth surface and the cementing residues ground.

It is also advantageous as a cost-effective and large-scale manufacture of the device can be achieved if the base body or the attachment body of the tooth attachment consists of plastic material.

By the use of a base and attachment body consisting of polycrystalline grains having X-ray visible precipitations, which is embedded or connected in a form-locking manner with an attachment or base body that consists of another material, a plurality of material combinations achieves an individual adaption to specific applications.

If the base body presents three-dimensionally arched contact surfaces, it is also advantageous since more strength is achieved at the joint where the device is connected with the tooth.

For the adhesive, a thickness structure distributed over the contact surface is achieved if a surface receiving an adhesive is provided with depressions, and thereby, besides the strength also an accordingly advantageous tenacity of the glued joint.

With arch-shaped recesses, slots, wings and/or hooks on the attachment body, a plurality of different joining, transition and contact points is achieved for the tension elements which are needed for the alignment.

The light transmission is further increased if the surface of the tooth attachment which consists of polycrystalline grains is chemically and/or mechanically polished.

A color adaptation or an opposing color effect is achieved if the ceramic base body presents a colored translucency.

The color of the translucent base body can be easily adapted or modified if the ceramic base body is provided with a metallic oxide, for example chromium oxide since the amount and kind of metallic oxide when oxygen is reduced, achieves easily different colors.

The invention will now be described further hereinafter, by way of example only, with reference to the accompanying drawings, in which.

Figure 1:
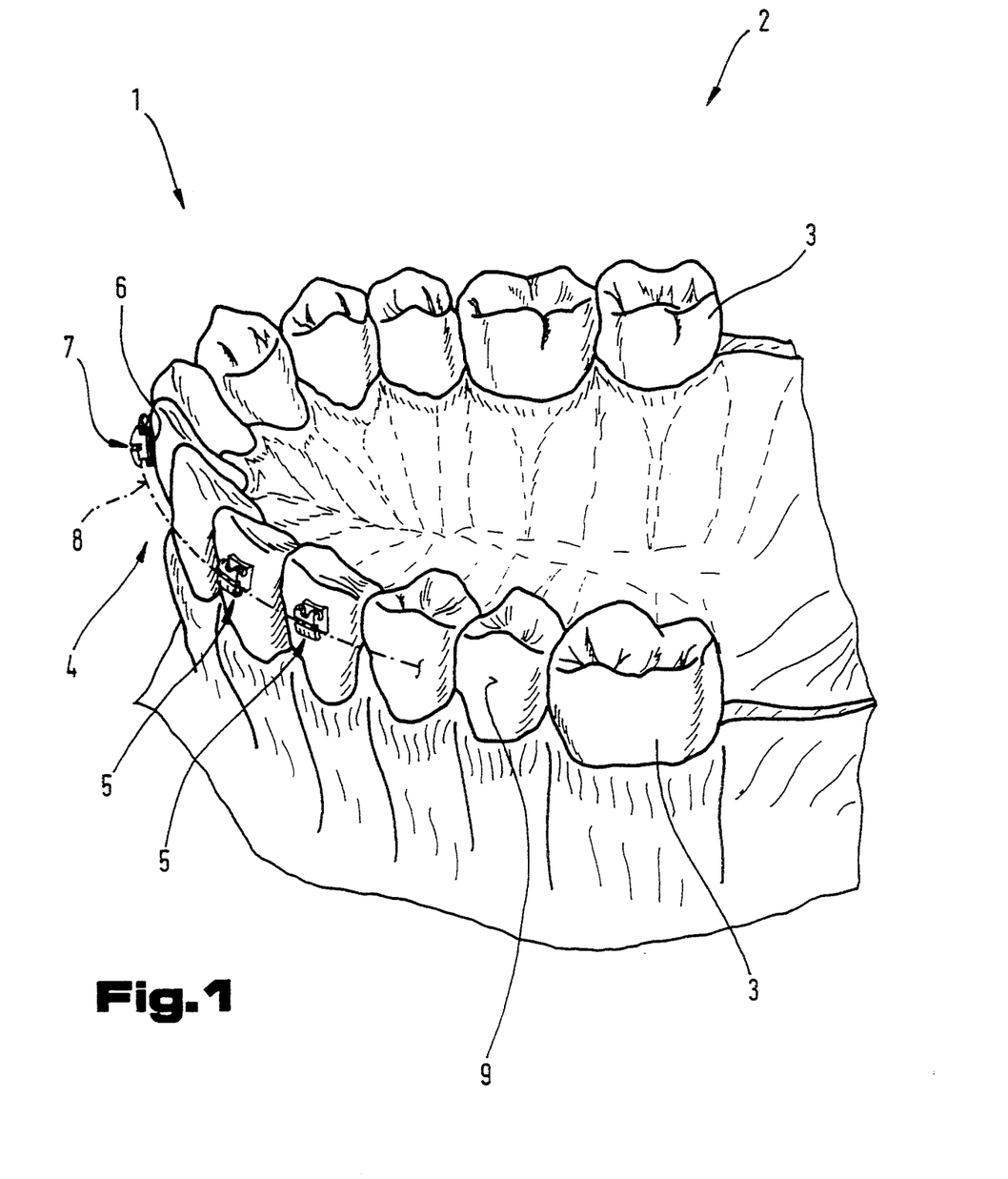
FIG. 1 is a simplified schematic illustration of a part of a set of teeth with an orthodontic device arranged thereon in accordance with the invention.

FIG. 1 shows a part of a lower jaw 1 with a set 2 of teeth 3. To urge teeth 3 into correct alignment an orthodontic device 4 is provided. The latter consists of schematically indicated tooth attachments 5 which are motionally connected with the teeth 3 by means of an adhesive layer. These tooth attachments 5 are provided with a recess 7 in which arch-wires 8 are inserted that pull the tooth attachments 5 into the desired position.

When the permanent load exerted on the teeth 3 achieves an alignment of these teeth 3 into the desired arrangement, the arch-wire 8 is removed and the tooth attachments 5 are cracked off from the surface 9 of the teeth 3 and the surface 9 of the teeth 3 is re-polished.

Figure 2:
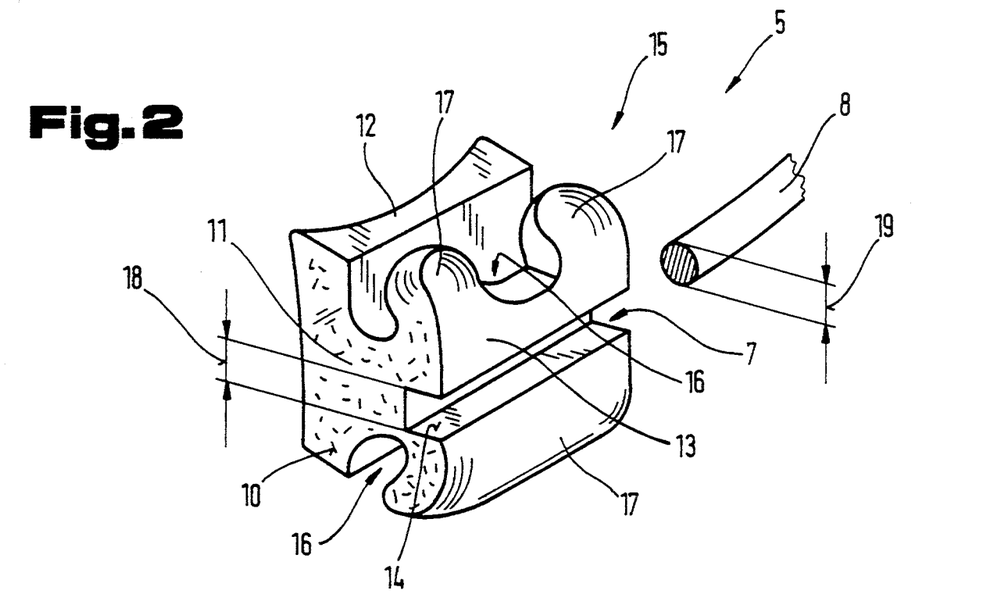
FIG. 2 is an enlarged, diagrammatical illustration of a tooth attachment of the orthodontic device shown in FIG. 1.

FIG. 2 shows such an enlarged tooth attachment 5 which has been produced from ceramic material 10. The one-piece base body 11 of the tooth attachment 5 shows a holding part 12 and a guiding part 13. The guiding pan 13 is provided with a longitudinal slot 14 and shows in the comer regions 15 of the latter or over the recesses 16 running parallel to the longitudinal slot 14 protruding extensions 17.

Preferably, the longitudinal slot 14 presents a rectangular cross-section wherein a width 18 transverse to the longitudinal slot 14 is slightly less than a diameter or a suitable parallel thickness 19 of the arch-wire 8.

As shown in FIG. 1, the holding part 12 is motionally connected with the lingual or labial surface 9 of the tooth 3 by means of an adhesive layer 6. The selection of the surface 9 to which the tooth attachment 5 is to be fastened, depends on the alignment method in use.

Figure 3:
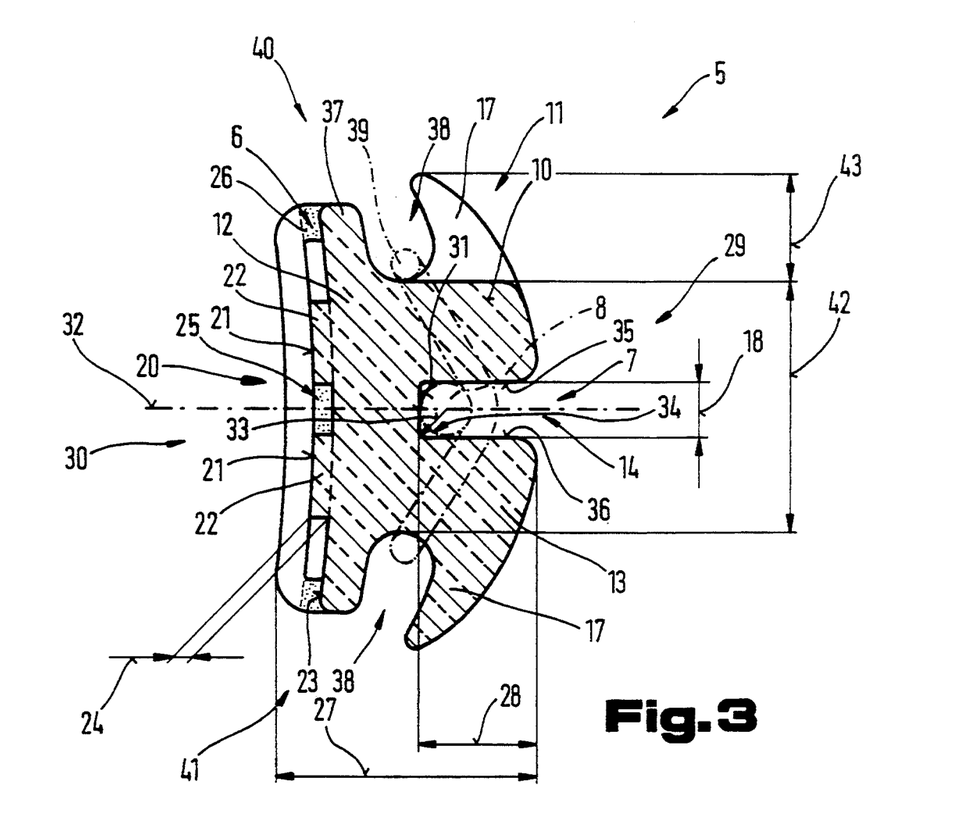
FIG. 3 is a sectional from view of the tooth attachment according to FIG. 2 greatly enlarged with a schematically illustrated structure.

FIG. 3 shows a sectional front view of the base body 11. A surface 20 of the holding part 12 is provided with inclined, arched or three-dimensionally formed contact surface 21 to allow for an adaptation to the different surface forms of the teeth 3. The contact surface 21 is arranged on raised parts 22, which project beyond an area 23 of the base body 11 by a distance 24 in the direction of the tooth 3. The individual protruding parts 22 are arranged in a distributed manner over the area 23, which causes the formation of depressions 25 between them, which serve to receive an adhesive 26 for the joining of the tooth attachment 5 with the tooth 3. The adhesive 26 of the adhesive layer 6 is here schematically indicated by dots in the sectional view. In order that the wearer of such a tooth attachment 5 has no disturbing feeling when wearing the orthodontic device 4, the tooth attachment 5 presents only a slight thickness 27 from the moth 3 in the direction of the arch-wire 8, which is indicated by dash-and-dot lines in the recess 7 of the longitudinal slot 14. A depth 28 of the longitudinal slot 14 is formed in such a way that on the one hand, the material 10 of the base body 11 has still enough strength to transmit the corrective forces from the arch-wire 8 to the tooth 3, and on the other hand does not result in too great a distance of the arch-wire 8 from the surface 9 of the tooth 3. The depth 28 of the longitudinal slot 14 is thereby extending from a front side 29 of the tooth attachment 5 in the direction of a tooth side 30.

A surface of the base 31 which extends into the depth 28 of the recess 7 approximately rectangular to a symmetrical plane 32 in the longitudinal direction of the longitudinal slot 14, presents with a radius 33 rounded corner regions 34 in the direction of the side surfaces 35, 36 that are formed by the longitudinal slot 14 and arranged apart from one another parallel to the symmetrical plane 32 in the width 18. Preferably, the radius 33 is less than half of the diameter of the arch-wire 8 which forms the thickness 19.

On both sides of the symmetrical plane 32 the guiding pan 13 of the tooth attachment 5 shows the above described extensions 17. Between the extensions 17 on the front side 29 and a web 37 of the holding part 12 on the tooth side 30, parallel to the longitudinal slot 14, provision is made for an accommodation 38 to hold a fixing element 39, which is shown schematically by dash-and-dot lines. The accommodations 38 for the fixing element 39 extend form an upper side 40 and also from a lower side 41 of the tooth attachment 5 in the direction of the symmetrical plane 32 up to a location 42 of the base body 11. Starting from the location 42 the extensions 17 project beyond the accommodations 38 by a height 43, which must be designed in such a way that a safe support of the fixing element 39 is guaranteed.

In order to exert a tensile strength from the tooth attachment 5 of the orthodontic device 4 to the tooth 3 by means of an arch-wire 8 in the direction of the front side 29, the fixing element 39 is inserted along the accommodations 38 and arranged in the direction of the symmetrical plane 32 so as to span the arch-wire 8 from the front side 29. This embodiment allows for secure positioning of the arch-wire 8 in the longitudinal slot 14.

Figure 4:
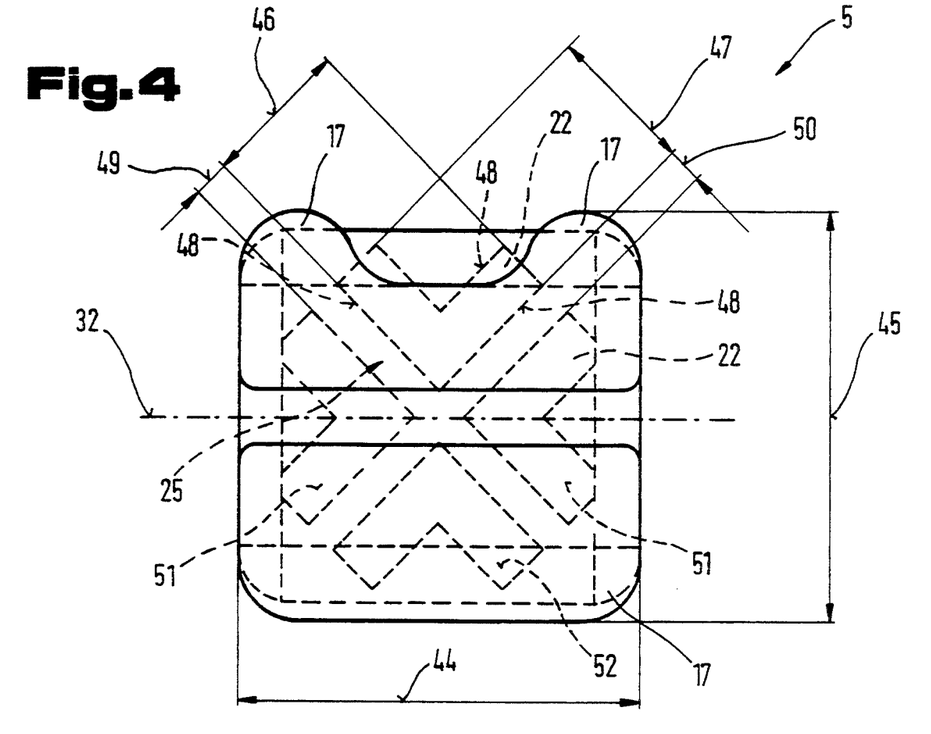
FIG. 4 is a side view of the tooth attachment according to FIG. 2.
Figure 5:
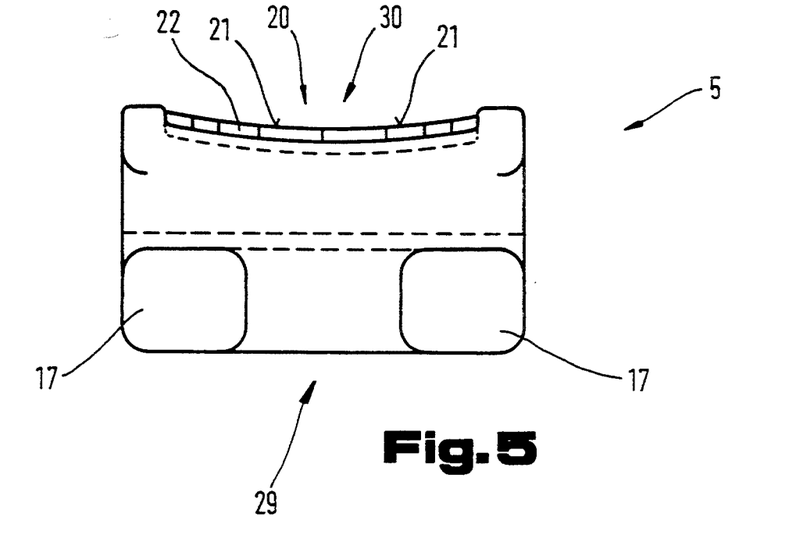
FIG. 5 is a top view of the tooth attachment according to FIG. 2.

FIGS. 4 and 5 show the tooth attachment from different sides. Thereby, the tooth attachment 5 shows in the direction of the symmetrical plane 32 a length 44 and a height 45 which extends approximately rectangular to the symmetrical plane 32. The raised parts 22 arranged on the tooth side 30 of the tooth attachment 5 together with their contact surfaces 21 have in the present embodiment about a V-shaped cross-section with lengths 46, 47 whereby the lateral edges 48 are offset by an angle of approximately 45° opposite the symmetrical plane 32. To achieve good adaptation to the different forms of teeth 3, the contact surfaces 21 of the raised parts 22 are formed in a three-dimensional shape.

Each of the lateral edges 48 of the individual raised parts 22 are spaced from one another by distances 49, 50 and thus, are forming surfaces 51, 52 in a V-shaped grid arrangement. This causes the formation of the required depressions 25 to receive the adhesive 26 on the tooth side 30 of the tooth attachment 5 between the surfaces 51, 52.

Figure 6:
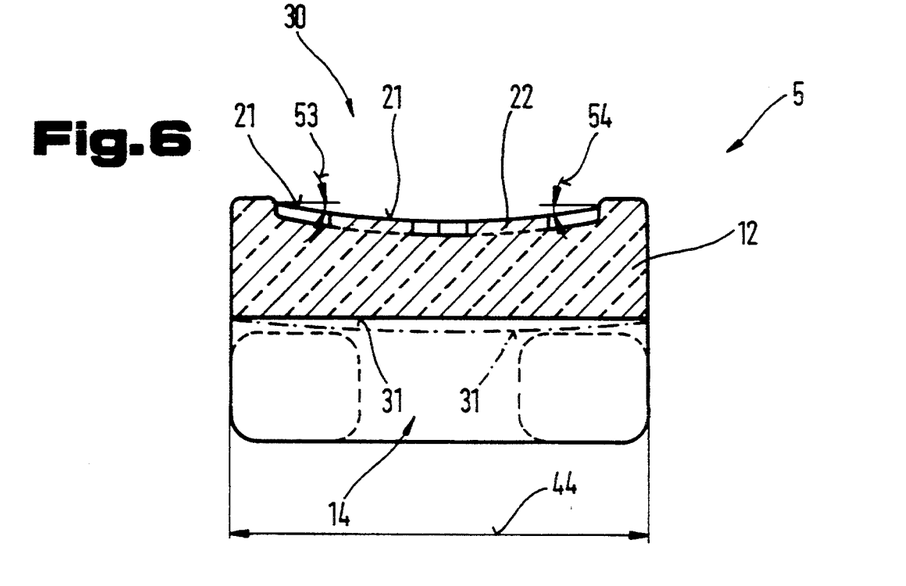
FIG. 6 is a sectional top view of the moth attachment according to FIG. 2.

FIG. 6 shows a section of the tooth attachment 5 in the symmetrical plane 32. Thereby, the embodiment of the three-dimensionally arched contact surfaces 21 on the raised parts 22 on the tooth side 30 can be seen very well.

In this embodiment the contact surfaces 21 are arranged in a pivotable manner on a reference plane parallel to the base 31 round an angle 53, 54.

In the present embodiment, the base 31 of the longitudinal slot 14 is formed in a straight line over the length 44 of the tooth attachment 5. However, it is also possible, as schematically indicated by dash-and-dot lines, to develop the base 31 in the form of a section of a circle, an ellipse or another curved form. This depends on both, the cooperation of the arch-wire 8 with the longitudinal slot 14, as well as on the desired purpose of use of the orthodontic device 4.

Figure 7:
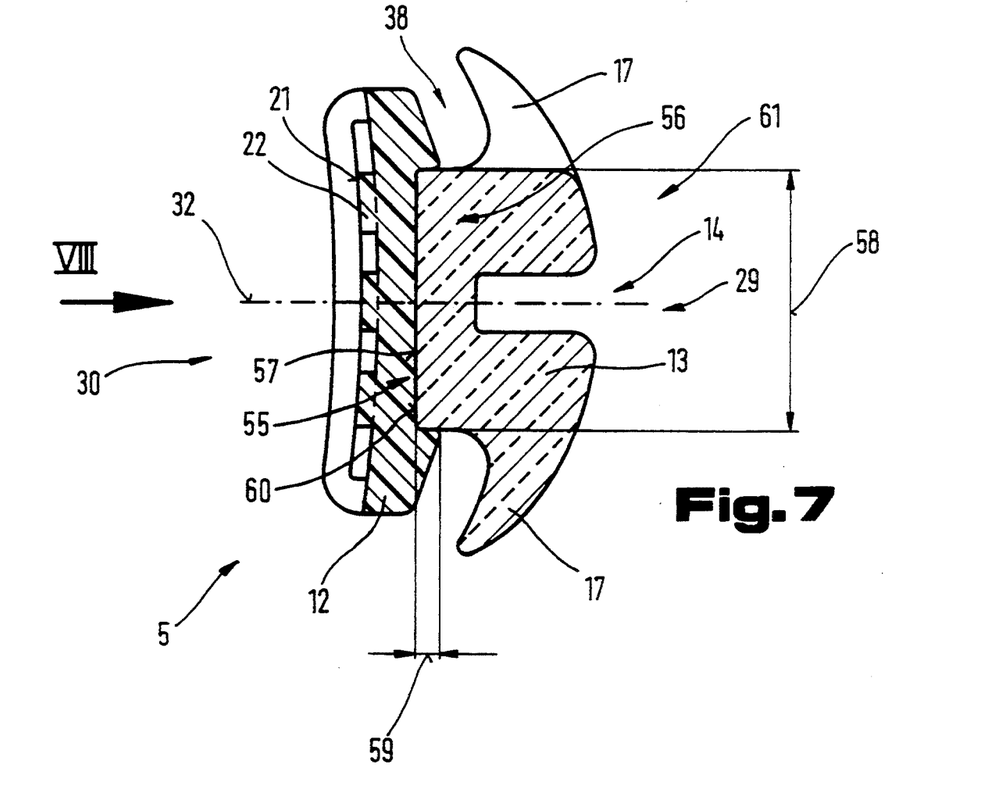
FIG. 7 is a front view of another variant of an embodiment of a tooth attachment in several parts in accordance with the invention.

FIG. 7 shows a variant of the embodiment of the tooth attachment 5, wherein the latter consists of several parts. Thereby, the holding part 12 is preferably made of plastic material and the guiding part 13 preferably of ceramic material. A transition area 55 between the holding part 12 and the guiding part 13 is a kind of groove and tongue connection 56, wherein a groove 57 in the holding part 12 shows both, a width 58 and also a depth 59.

The holding part 12 can be produced for example by an extrusion molding method, injection molding or the like, wherein the tooth side 30 may receive its appropriate form by a subsequent treatment of its own and is joined to form a unit with the help of the adhesive layer 60 with the finished ceramic guiding part 13, which forms an attachment body 61. The connection between the holding part 12 and the attachment body 61 can also take place by a welding process or in a form-locking manner, for example.

The form-shaped embodiment of the extensions 17, the longitudinal slot 14, the accommodations 38 and the raised parts 22 together with the contact surfaces 21 may be the same than those described in the above embodiments.

Figure 8:
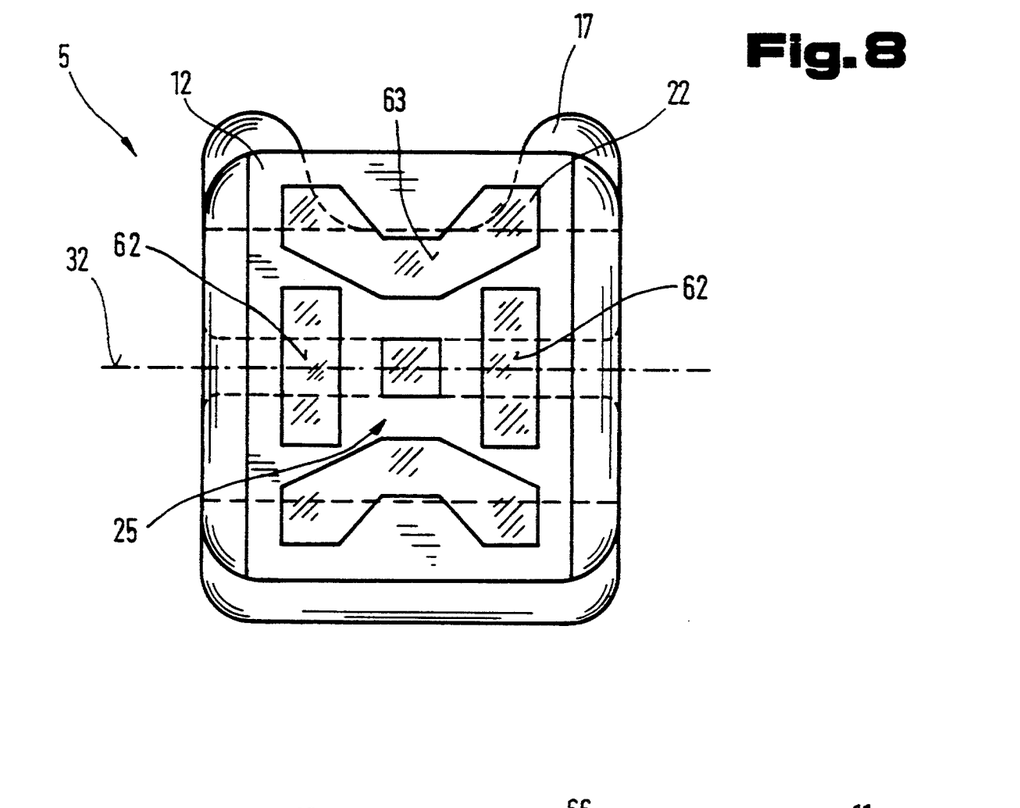
FIG. 8 is a view of the tooth attachment according to arrow VIII in FIG. 7.

FIG. 8 shows the tooth side 30 of the holding part 12 of the moth attachment 5. The raised parts 22 present an approximately V-shaped or rectangualr arrangement. By an arrangement of the raised parts 22 on the tooth side 30 of the tooth attachment 5, contact surfaces 62, 63 are formed, between of which the depressions 25 are arranged which receive the adhesive 26.

Figure 9:
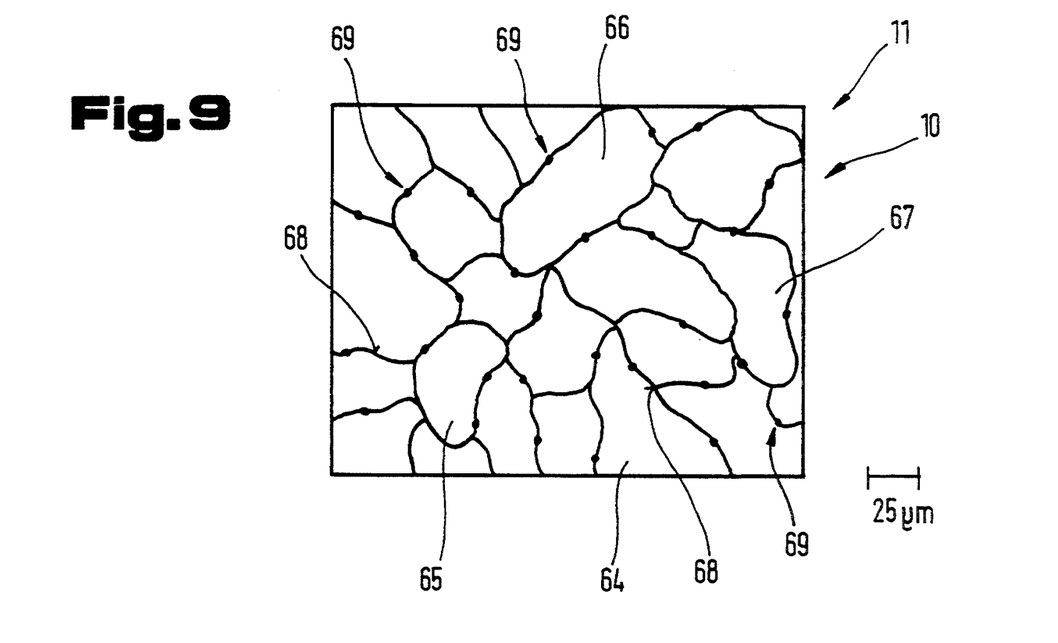
FIG. 9 is a greatly enlarged top view with the schematically illustrated structure of a part of a section of a tooth attachment in accordance with the invention.

FIG. 9 shows a greatly enlarged illustration of the fine structure of the structural development of the base body 11 made of ceramic material. The material 10 is composed of the individual grains 64 to 67, wherein on the grain boundaries 68 precipitations 69 are forming, which in contrast to the grains 64 to 67 can be seen when X-rayed. This is why it is now possible, if for example a part of the tooth attachment 5 of such an orthodontic device 4 comes unintentionally into the body of the wearer, to trace this part in the body by means of X-rays.

In the described tooth attachment 5, the base body 11 consists of ceramic material.

The production of the base body 11 or the holding or attachment part of ceramic material can thereby occur according to known methods from prior art, as described among others in U.S. Pat. Nos. 3,026,210, 3,026,177, 4,150,317 and 4,954,080.

Tooth attachments 5 of ceramic material are usually produced from high purity aluminum oxide powder, a binding agent, additives to limit grain growth, and X-ray opaque oxides. The mass produced in such a manner is deformed to a green body in the desired mold. The dry powder is thereby pressed with a powder compaction press into a cavity. However, it is also possible to deform the semi-dried material into the desired shapes of the body by an extrusion molding method or injection molding. Another preferred method is to extrude the ceramic base material into the desired form, which allows for a final, mechanical formation before and after the sintering process.

The green body is then preheated in an oxidizing environment for approximately 1 hour at a temperature of 1,200° C., so that the green body presents enough strength to be treated mechanically or for the transfer to the sintering process.

The sintering of the green body to the desired density can occur in a reduction environment, such as hydrogen at a temperature in the range of from 1,750° to 1,950° C. The sintering time is 45 minutes to several hours in order to achieve an average grain size in the range from 5 to 40 micrometers and a desired light transmission. A slice of the finished base body 11 with a thickness of 0.5 mm should have a light transmission in the visible spectrum having a wavelength of 0.3 to 0.8 microns, i.e. from 5 to 45%. In order to reduce the porosity of the base body, hot isostatic pressing occurs wherein for a certain period of time at a temperature in the range of from 1,450° and 1,580° C. a pressure of approximately 30,000 psi is applied to reduce the portion of pores in the base body 11 $V_p$ below 0.0003.

In order to provide the finished product with a smooth surface, the latter can be polished mechanically or chemically as described among others in the U.S. Pat. No. 4,079,167. This can also increase the optical transmittance of the tooth attachment 5. To create a polycrystalline base body 11 in accordance with the present invention with an adequate X-ray opaque embodiment and optical properties, a high purity aluminum oxide powder is used with a percentage purity of more than 99.98% and a grain size in the range of from 0.050 to 0.15 microns and an agglomerate distribution of less than 5 micrometers.

To the above mentioned aluminum powder, a magnesium oxide in the range of from below 0.1% by weight is added, to prevent the formation of a magnesium-aluminum-spinel type phase (Mg $Al_2O_4$) and at the same time limiting grain growth.

Furthermore, a magnesium fluoride in an adequate range of from 0.01 and 0.5% by weight is also added to the above mentioned mixture. This magnesium fluoride limits also grain growth in an early phase of the sintering process and is vaporized in a subsequent phase of the firing process. It is, however, also advantageous, if a portion of 5 to 15 ppm high purity lanthanum oxide is added which leads to improved light transmission of the tooth attachment in the magnesium-aluminum-spinel type phase.

The desired X-ray opaque embodiment of the base body 11 is achieved by adding an amount of 3 to 150 ppm ytterbium fluoride with a purity percentage of more than 99% and a grain size distribution of less than 7 micrometers, and also 60 to 120 ppm high purity yttrium oxide as well as 3 to 30 ppm high purity lanthanum oxide. It is also possible to use a small amount of a suitable organic binding agent to provide this overall mixture with sufficient strength in the green phase.

For color coordinatination a metallic oxide, for example a chromium oxide is added to the starting materials for the production of the base body 11 in order to achieve the desired appearance. Thus, the different shades of color of the teeth 3 can be taken into account for the wearer of such an orthodontic device 4. It is however also possible to create tooth attachments 5 with different colors by adding different sorts of metallic oxides.

The individual, above described examples of embodiments and the variants shown in these embodiments and the different embodiments can of course also form their own solutions in accordance with the invention and can be combined in any way possible.

Finally, it should be indicated for good order's sake that for improved understanding of the function of the orthodontic device many of its parts have been schematically and unproportionally enlarged.

I claim:

1. An orthodontic device comprising a ceramic tooth attachment, the ceramic tooth attachment comprising a base body having an in-line transmittance of visible light in the range of 5% to 60% through a thickness of 0.5 mm and the base body consisting of
   (a) polycrystalline grains comprising a substance selected from the group consisting of high purity zircon, high purity yttrium oxide, lead titanate zirconate and an aluminum oxide, and
   (b) X-ray visible precipitations arranged on grain boundaries between the polycrystalline grains, the precipitations comprising ytterbium fluoride in a concentration range of 3 to 150 ppm.

2. The orthodontic device of claim 1, wherein the polycrystalline grains comprise an aluminum oxide, and high purity yttrium oxide is added thereto in a concentration range of 60 to 120 ppm.

3. The orthodontic device of claim 1, wherein the polycrystalline grains comprise an aluminum oxide, and high purity lanthanum oxide is added thereto in a concentration range of 3 to 30 ppm.

4. The orthodontic device of claim 1, wherein the ceramic tooth attachment is fired and the average grain size is in the range of 5 to 90 micrometers.

5. The orthodontic device of claim 1, wherein the base body has pores occupying a volume of less than 0.003% of the base body volume.

6. The orthodontic device of claim 1, wherein the polycrystalline grains comprise an aluminum oxide, and a grain-growth limiting additive comprising less than 0.1% by weight, of high purity magnesium oxide is added thereto.

7. The orthodontic device of claim 1, wherein the polycrystalline grains comprise an aluminum oxide, and a grain-growth limiting additive comprising 0.01% to 0.5%, by weight, of magnesium fluoride is added thereto.

8. The orthodontic device of claim 1, wherein the base body comprises lithium fluoride in a concentration range of 5 ppm to 15 ppm.

9. The orthodontic device of claim 1 wherein the polycrystalline grains comprise a mixture of lead titanate zirconate, lanthanum oxide in a concentration range of 3 ppm to 150 ppm, and yttrium oxide in a concentration range of 3 ppm to 30 ppm.

10. The orthodontic device of claim 1, wherein the base body consists of an aluminum oxide polycrystalline stabilized zircon ceramic and yttrium fluoride and lanthanum oxide additives.

11. The orthodontic device of claim 1, wherein the base body comprises an attachment part of the tooth attachment, and the tooth attachment further comprises a second part formed of a material different from that of the base body.

12. The orthodontic device of claim 11, wherein the second part consists of a plastic material.

13. The orthodontic device of claim 11, wherein the attachment part is connected frictionally with the second part.

14. The orthodontic device of claim 1, wherein the base body constitutes an attachment part and has three-dimensionally arched contact surfaces.

15. The orthodontic device of claim 14, wherein the surfaces define at least one depression for receiving an adhesive.

16. The orthodontic device of claim 14, wherein the contact surfaces are polished.

17. The orthodontic device of claim 1, wherein the base body has a colored translucency.

18. The orthodontic device of claim 1, wherein a metallic oxide is added to the base body to provide color.

19. The orthodontic device of claim 18, wherein the metallic oxide is a chromium oxide.

* * * * *